US010412996B2

(12) United States Patent
Bright et al.

(10) Patent No.: US 10,412,996 B2

(45) Date of Patent: Sep. 17, 2019

(54) CARTRIDGE FOR PUMP-OPERATED AEROSOL-GENERATING SYSTEM

(71) Applicant: Altria Client Services LLC, Richmond, VA (US)

(72) Inventors: Ben Bright, Gloucestershire (GB); Ben Mazur, Bristol (GB)

(73) Assignee: Altria Client Services LLC, Richmond, VA (US)

( * ) Notice: Subject to any disclaimer, the term of this patent is extended or adjusted under 35 U.S.C. 154(b) by 323 days.

(21) Appl. No.: 15/388,641

(22) Filed: Dec. 22, 2016

(65) Prior Publication Data

US 2017/0172210 A1 Jun. 22, 2017

Related U.S. Application Data

(63) Continuation of application No. PCT/EP2016/077681, filed on Nov. 15, 2016.

(30) Foreign Application Priority Data

Dec. 22, 2015 (EP) .................................... 15202075

(51) Int. Cl.
*A61M 15/06* (2006.01)
*A24F 47/00* (2006.01)
(Continued)

(52) U.S. Cl.
CPC ......... *A24F 47/008* (2013.01); *H05B 1/0244* (2013.01); *B05B 7/0012* (2013.01); (Continued)

(58) Field of Classification Search
None
See application file for complete search history.

(56) References Cited

U.S. PATENT DOCUMENTS 2,835,781 A * 5/1958 Bashuk ................ A61M 11/041 219/552
6,234,167 B1 * 5/2001 Cox .................. A61M 15/0083 128/200.14
(Continued)

FOREIGN PATENT DOCUMENTS

EP 1618803 A1 1/2006
WO WO-2013/050934 A1 4/2013
(Continued)

OTHER PUBLICATIONS

Extended European Search Report for European Patent Application No. 15202075.6 dated Jun. 6, 2016.
(Continued)

*Primary Examiner* — Thor S Campbell
(74) *Attorney, Agent, or Firm* — Harness, Dickey & Pierce, P.L.C.

(57) ABSTRACT

An electrically operated aerosol-generating system may include a reservoir configured to hold a liquid aerosol-forming substrate, an atomizer assembly configured to vaporize the liquid aerosol-forming substrate to form an aerosol, and a pump configured to convey the liquid aerosol-forming substrate from the reservoir to the atomizer assembly. The reservoir may include a substantially rigid housing and an inlet valve that is configured to allow air into the reservoir based on a pressure difference between an interior of the housing and an exterior of the housing exceeding a threshold pressure difference. This improves the reliability and efficiency of delivery of liquid to the wick. The system may further include a robust reservoir that is configured to at least partially mitigate liquid leakage between the reservoir interior and the reservoir exterior.

20 Claims, 2 Drawing Sheets

(51) Int. Cl.
*H05B 1/02* (2006.01)
*B05B 7/16* (2006.01)
*B05B 7/00* (2006.01)

(52) U.S. Cl.
CPC ...... *B05B 7/1686* (2013.01); *H05B 2203/021* (2013.01); *H05B 2203/022* (2013.01)

(56) References Cited

U.S. PATENT DOCUMENTS 8,511,318 B2* 8/2013 Hon ...................... A24F 47/002 131/273
2003/0132219 A1* 7/2003 Cox ..................... A61M 11/041 219/486
2004/0081624 A1* 4/2004 Nguyen ............... A61K 9/0078 424/44
2008/0085103 A1* 4/2008 Beland .................... A61L 9/035 392/390
2008/0257915 A1 10/2008 Wold
2009/0236374 A1* 9/2009 Pardes .................. A61F 9/0008 222/494
2012/0090630 A1* 4/2012 Hon ...................... A24F 47/002 131/273
2012/0230659 A1* 9/2012 Goodman ............... F22B 1/282 392/395
2015/0020822 A1 1/2015 Janardhan et al.
2015/0027456 A1* 1/2015 Janardhan ............. A24F 47/008 131/328
2015/0047662 A1* 2/2015 Hopps ................... A24F 47/008 131/329
2015/0216237 A1* 8/2015 Wensley ............... A24F 47/008 131/273
2017/0020192 A1* 1/2017 Fregonese ............ H05B 3/0014

FOREIGN PATENT DOCUMENTS

WO WO-2014/150552 A1 9/2014
WO WO-2014/153515 A1 9/2014
WO WO-2016/096762 A1 6/2016

OTHER PUBLICATIONS

International Preliminary Report dated Jun. 26, 2018 issued in corresponding International Application No. PCT/EP2016/077681.
Written Opinion of the International Search Authority dated May 30, 2017 issued in corresponding International Application No. PCT/EP2016/077681.
International Search Report dated May 30, 2017 issued in corresponding International Application No. PCT/EP2016/077681.

* cited by examiner

CARTRIDGE FOR PUMP-OPERATED AEROSOL-GENERATING SYSTEM

CROSS-REFERENCE TO RELATED APPLICATIONS

This application is a continuation of, and claims priority to, international application no. PCT/EP2016/077681, filed on Nov. 15, 2016, and further claims priority under 35 U.S.C. § 119 to European Patent Application No. 15202075.6, filed Dec. 22, 2015, the entire contents of each of which are incorporated herein by reference.

BACKGROUND

Field

One or more example embodiments relate to electrically operated aerosol-generating systems, including electronic vaping devices, configured to actively pump a liquid from a reservoir to a vaporizer.

Description of Related Art

Liquid based, electrically heated vaping systems, including electrically-operated aerosol-generating systems, also referred to herein as electronic vaping devices, are becoming increasingly popular. In some cases, one or more of these systems comprise a liquid store, an electric heater and a capillary wick that conveys liquid from the liquid store to the heater, together with a power supply and electric circuitry. The heater may include a coil of wire wrapped around the capillary wick and may generate heat based on resistive heating. The liquid in the capillary wick is vaporized by the heater to form a vapor. An adult vaper may draw on the system to cause air to flow past the heater. The airflow past the heater may entrain the generated vapor. The generated vapor may subsequently cool within the airflow to form an aerosol.

The liquid store may be a refillable or replaceable cartridge that is fixed to, or inserted into, a remainder of the aerosol-generating system. The cartridge may also include the wick and heater. In some cases, the wick and heater may be provided in an atomizer assembly that is separate to the cartridge.

The liquid store, also referred to herein as a liquid reservoir, a reservoir, or the like, may include a sealed enclosure and a rigid housing, such that the liquid reservoir is configured to mitigate liquid leakage from the reservoir before or during vaping, thereby improving the adult vaper experience and improving stability and performance of the aerosol-generating system itself (e.g., circuitry included therein). So the liquid reservoir may be a fully sealed and robust container.

In some cases, an internal pressure of the reservoir may vary with the amount of liquid stored therein, based on the fixed volume of the liquid reservoir. For example, as liquid is conveyed to the wick, the internal pressure of the liquid reservoir may decrease. The rate of conveyance of liquid from the liquid reservoir to the wick may decrease with the decrease in reservoir internal pressure. In some cases, air may enter the reservoir through the wick, based, for example, on the internal pressure of the reservoir decreasing below an ambient pressure, such that the pressure inside and outside of the reservoir is balanced. Such an air flow through the wick may affect the performance of the wick to convey liquid from the reservoir and may affect one or more parameters associated with the generated vapor (e.g., density and flavor).

SUMMARY

According to some example embodiments, a cartridge for an electrically operated aerosol-generating system may include: a liquid reservoir configured to hold a liquid aerosol-forming substrate. The reservoir may include a rigid housing, an air inlet valve configured to allow air into the liquid reservoir based on a pressure difference between an interior of the reservoir and an exterior of the reservoir exceeding a threshold pressure difference, and an outlet extending through the rigid housing, the outlet configured to engage with a pump of the electrically operated aerosol-generating system, such that the outlet is configured to direct liquid aerosol-forming substrate out of the reservoir.

The liquid reservoir may include a filling port in the rigid housing, and the filling port may be configured to direct liquid aerosol-forming substrate into the interior of the reservoir.

The outlet may be configured to be sealed prior to engagement with the pump.

The cartridge may include the pump.

The cartridge may include a vaporizer, wherein the pump is between the liquid reservoir and the vaporizer, and the pump is configured to convey liquid aerosol-forming substrate from the liquid reservoir to the vaporizer.

The vaporizer may include an electrical heater.

The vaporizer may include a capillary material configured to convey liquid aerosol-forming substrate to the electrical heater.

The pump may be a piezoelectric micropump.

The inlet valve may be a check valve.

The check valve may be one of a ball check valve and a duckbill check valve.

According to some example embodiments, an electrically operated aerosol-generating system may include: a housing configured to define an interior space, a cartridge within the interior of the housing, a vaporizer within the interior of the housing, and a pump connected to an outlet of the cartridge. The housing may include an air inlet configured to direct air into the interior of the housing, and an air outlet configured to direct at least air out of the interior of the housing. The cartridge may include a liquid reservoir configured to hold a liquid aerosol-forming substrate. The reservoir may include a rigid housing, an air inlet valve configured to allow air into the liquid reservoir from an interior of the housing of the aerosol-generating system based on a pressure difference between an interior of the reservoir and an exterior of the reservoir exceeding a threshold pressure difference, and an outlet extending through the rigid housing. The vaporizer configured to vaporize the liquid aerosol-forming substrate. The pump may be configured to convey liquid aerosol-forming substrate from the reservoir to the vaporizer.

The pump may be a piezoelectric micropump.

The vaporizer may include an electrical heater.

The aerosol-generating system may include a power supply configured to supply electrical power to the pump and the vaporizer.

The aerosol-generating system may include control circuitry configured to activate the pump based on a determination that the vaporizer is activated.

The aerosol-generating system may be a hand held aerosol-generating system.

According to some example embodiments, a method may include: conveying a liquid aerosol-forming substrate out of a reservoir based on operation of a pump, the reservoir including a rigid housing held within a housing of an aerosol-generating system, the reservoir configured to hold the liquid aerosol-forming substrate, the conveying including conveying the liquid aerosol-forming substrate through an outlet extending through the rigid housing; and allowing air into the reservoir from an interior of the housing of the aerosol-generating system through the rigid housing based on a pressure difference between an interior of the reservoir and an exterior of the reservoir exceeding a threshold pressure difference.

The conveying may include conveying the liquid aerosol-forming substrate from the reservoir to a vaporizer, the vaporizer configured to vaporize the liquid aerosol-forming substrate based on generating heat.

The conveying may further include selectively controlling a particular supply of electrical power to the pump based on a determination that the vaporizer is activated.

The conveying may further include selectively controlling a separate supply of electrical power to the vaporizer, such that the vaporizer is activated, based on a determination that a flow rate of air detected by a flow sensor exceeds a threshold flow rate.

Some example embodiments include an electrically-operated aerosol-generating system that comprises: a liquid reservoir comprising a rigid housing; an air inlet valve in the rigid housing, the air inlet valve configured to allow air into the liquid reservoir when a pressure difference between outside of the housing and inside of the housing exceeds a threshold pressure difference; a vaporizer configured to vaporize the liquid; and a pump connected to an outlet through the rigid housing and configured to pump liquid from the liquid reservoir to the vaporizer.

The use of a pump between the liquid reservoir and the vaporizer may improve the reliability and efficiency of delivery of liquid to the vaporizer. In addition, some example embodiments may include an air inlet valve in the liquid reservoir. This may allow the pressure inside the reservoir to equalize with atmospheric pressure. This in turn may allow a rigid reservoir housing to be used, providing the necessary robustness for the liquid reservoir, particularly for a refillable reservoir without the problem of reduced pressure in the reservoir.

The liquid reservoir of the aerosol-generating system may have a rigid housing. As used herein, the term ‘rigid housing’ is used to mean a housing that is self-supporting. The housing may be substantially cylindrical. An opening for the air inlet valve may be provided at one end of the cylinder. The housing of the liquid storage portion may have a substantially circular cross section.

The liquid reservoir may further comprise a carrier material within the housing for holding the liquid. The liquid may be adsorbed or otherwise loaded onto a carrier or support. The carrier material may be made from any suitable absorbent plug or body, for example, a foamed metal or plastics material, polypropylene, terylene, nylon fibers or ceramic.

The pump may be a micropump, such as a piezoelectric micropump.

The valve may be a check valve, such as a ball check valve or a duckbill check valve. The valve may be push fit to the housing of the liquid reservoir.

The system may comprise a capillary material positioned between the pump and the vaporizer. The capillary material may have a fibrous or spongy structure. The capillary material may include a bundle of capillaries. For example, the capillary material may comprise a plurality of fibers or threads or other fine bore tubes. The fibers or threads may be generally aligned to convey liquid to the heater. The capillary material may comprise sponge-like or foam-like material. The structure of the capillary material forms a plurality of small bores or tubes, through which the liquid can be transported by capillary action. The capillary material may comprise any suitable material or combination of materials. Examples of suitable materials are a sponge or foam material, ceramic- or graphite-based materials in the form of fibers or sintered powders, foamed metal or plastics materials, a fibrous material, for example made of spun or extruded fibers, such as cellulose acetate, polyester, or bonded polyolefin, polyethylene, terylene or polypropylene fibers, nylon fibers or ceramic. The capillary material may have any suitable capillarity and porosity so as to be used with different liquid physical properties. The liquid has physical properties, including but not limited to viscosity, surface tension, density, thermal conductivity, boiling point and vapor pressure, which allow the liquid to be transported through the capillary material by capillary action. The capillary material may be configured to convey the aerosol-forming substrate to the vaporizer. The capillary material may extend into interstices in the vaporizer.

The vaporizer may comprise an electrical heater. The electrical heater may be a coil of wire surrounding the capillary wick. The electrical heater may be a mesh heater. The mesh heater may be in contact with the capillary material. The electrical heater may be inductively heated or may be electrically connected to a power supply. The vaporizer may be a vibrating mesh or a vibrating diaphragm.

The system may comprise a power supply configured to supply power to operate the pump and the vaporizer. The power supply may be a battery. The battery may be a Lithium based battery, for example a Lithium-Cobalt, a Lithium-Iron-Phosphate, a Lithium Titanate or a Lithium-Polymer battery. The battery may be a Nickel-metal hydride battery or a Nickel cadmium battery. The power supply may be another form of charge storage device such as a capacitor. The power supply may be rechargeable and may be configured for many cycles of charge and discharge. The power supply may have a capacity that allows for the storage of enough energy for one or more generations of aerosol; for example, the power supply may have sufficient capacity to allow for the continuous generation of aerosol for a period of around six minutes, or for a period that is a multiple of six minutes. In some example embodiments, the power supply may have sufficient capacity to allow for a predetermined number of draws of air through the system or discrete activations of the heating means and actuating means.

The system may comprise electric circuitry. The electric circuitry may comprise a microprocessor, which may be a programmable microprocessor, a microcontroller, or an application specific integrated chip (ASIC) or other electronic circuitry capable of providing control. The electric circuitry may comprise further electronic components.

The electric circuitry may be configured to regulate a supply of power to the vaporizer. Power may be supplied to the vaporizer continuously following activation of the system or intermittently, such as on a puff-by-puff basis. The electric circuitry may be configured to regulate the supply of power to the pump.

The aerosol-generating system may comprise a puff detector (“sensor”) in communication with the electric circuitry. The detector may be configured to detect when an adult \Taper draws on the system. The electric circuitry may be configured to control power to the vaporizer in dependence on the input from the detector, or the pump, or both the pump and the vaporizer.

The aerosol-generating system may comprise an input, such as a switch or button. This enables the adult vapor to turn the system on. The switch or button may activate the vaporizer.

The electric circuitry may be configured to operate the pump based on activation of the vaporizer. For example the pump may be activated when the vaporizer is activated. The electric circuitry may be configured to operate the pump following activation of the vaporizer. For example, the vaporizer may be activated based on a sensed draw of air or based on another input. Activation of the vaporizer will deplete the liquid in the vicinity of the vaporizer. The pump may be controlled to supply more liquid to the vaporizer after a particular (or, alternatively, predetermined) duration of activation of the vaporizer. The electric circuitry may also be configured to operate the pump when the system is switched on. If there has been a significant period of time since the last use of the system, the vaporizer may have become dry, and so it may be beneficial to operate the pump prior to activation of the vaporizer.

The system may be an electrically operated vaping system. The system may be a handheld aerosol-generating system. The aerosol-generating system may have a total length between approximately 30 mm and approximately 150 mm. The system may have an external diameter between approximately 5 mm and approximately 30 mm.

The liquid in the liquid reservoir may comprise a plant-based material. The liquid may comprise tobacco. The liquid may comprise nicotine. The liquid may comprise a tobacco-containing material containing volatile tobacco flavor compounds, which are released from the liquid upon heating. The liquid may alternatively comprise a non-tobacco-containing material. The liquid may comprise homogenized plant-based material. The liquid may comprise homogenized tobacco material. The liquid may comprise at least one aerosol-former. An aerosol-former is any suitable known compound or mixture of compounds that, in use, facilitates formation of a dense and stable aerosol and that is substantially resistant to thermal degradation at the temperature of operation of the system. Suitable aerosol-formers are well known in the art and include, but are not limited to: polyhydric alcohols, such as triethylene glycol, 1,3-butanediol and glycerin; esters of polyhydric alcohols, such as glycerol mono-, di- or triacetate; and aliphatic esters of mono-, di- or polycarboxylic acids, such as dimethyl dodecanedioate and dimethyl tetradecanedioate. Preferred aerosol formers are polyhydric alcohols or mixtures thereof, such as triethylene glycol, 1,3-butanediol and, most preferred, glycerin. The liquid may comprise other additives and ingredients, such as flavorants.

In a second aspect, there is provided a cartridge for an electrically operated aerosol-generating system, comprising: a liquid reservoir comprising a rigid housing; an air inlet valve in the rigid housing, configured to allow air into the liquid reservoir when a pressure difference between outside of the housing and inside of the housing exceeds a threshold pressure difference; and an outlet through the rigid housing configured to engage a pump in the electrically operated aerosol-generating system.

The cartridge may comprise a filling port in the rigid housing through which liquid can pass into the liquid reservoir. The filling port may be sealed by a pierceable septum or by a removable plug.

The outlet may be sealed prior to engagement with the pump. For example, the cartridge may comprise a peelable or pierceable septum, foil or film that seals the outlet.

The cartridge may comprise the pump. The pump may be a piezoelectric micropump.

The cartridge may comprise a vaporizer. The pump may be connected between the liquid reservoir and the vaporizer and may be configured to pump liquid from the liquid reservoir to the vaporizer.

The vaporizer may comprise an electrical heater. The vaporizer may comprise a capillary material configured to convey the liquid from the pump to the electrical heater.

The valve may be a check valve, such as a ball check valve or a duckbill check valve.

The pump and vaporizer may be provided in an atomizer assembly separate to, but connectable with, the cartridge. The aerosol generating system may additionally comprise a main body comprising a power source and control circuitry. The main body may be connectable with the cartridge or an atomizer assembly.

Features described with reference to the first aspect of the invention may be applied to the second aspect of the invention.

BRIEF DESCRIPTION OF THE DRAWINGS

Example embodiments will be further described, by way of example only, with reference to the accompanying drawings, in which.

DETAILED DESCRIPTION

Figure 1:
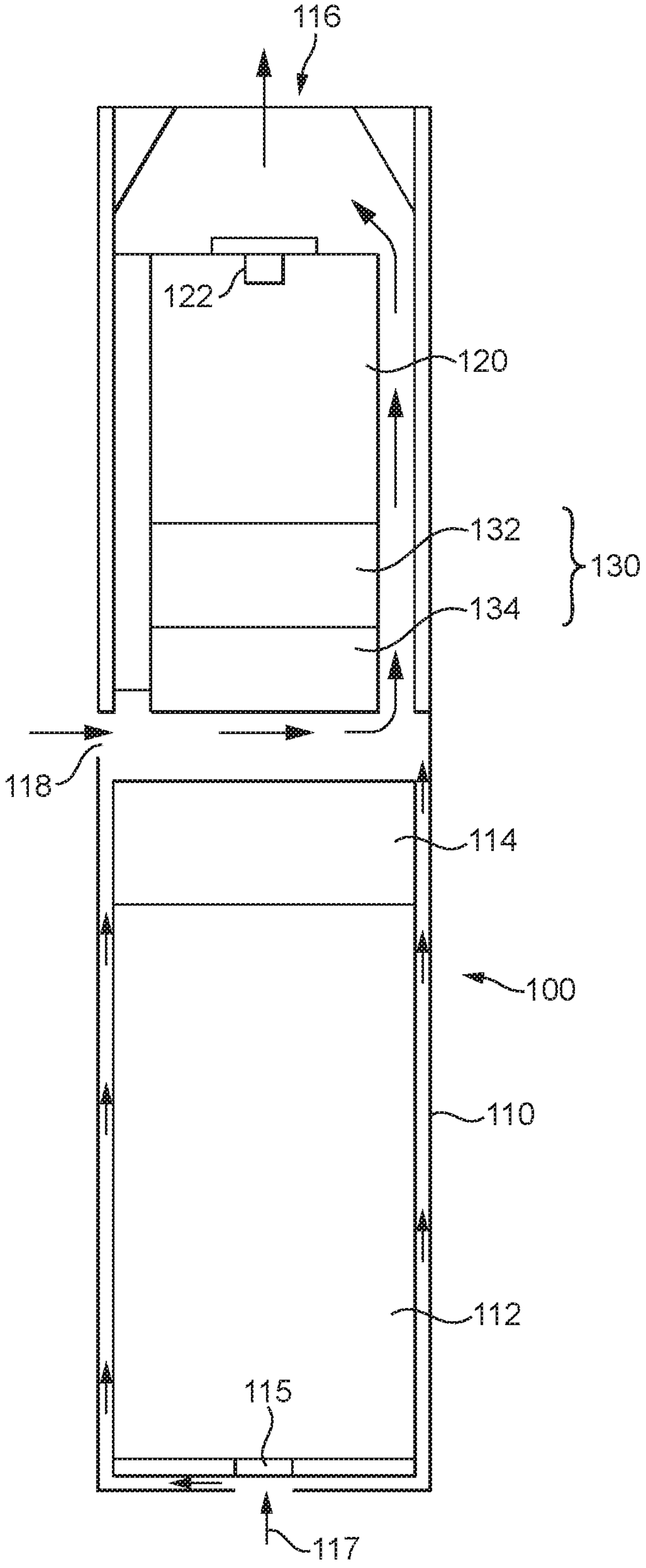
FIG. 1 is a schematic illustration of a first embodiment of an aerosol-generating system according to some example embodiments.

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms “a”, “an” and “the” are intended to include the plural forms as well, unless the context clearly indicates otherwise. It will be further understood that the terms “comprises,” “comprising,” “includes,” and/or “including,” when used in this specification, specify the presence of stated features, integers, steps, operations, and/or elements, but do not preclude the presence or addition of one or more other features, integers, steps, operations, elements, and/or groups thereof.

It will be understood that when an element or layer is referred to as being “on”, “connected to” or “coupled to” another element or layer, it can be directly on, connected or coupled to the other element or layer or intervening elements or layers may be present. In contrast, when an element is referred to as being “directly on”, “directly connected to” or “directly coupled to” another element or layer, there are no intervening elements or layers present. As used herein, the term "and/or" includes any and all combinations of one or more of the associated listed items.

It will be understood that, although the terms first, second, etc. may be used herein to describe various elements, regions, layers and/or sections, these elements, regions, layers acid/or sections should not be limited by these terms. These terms are only used to distinguish one element, region, layer or section from another region, layer or section. Thus, a first element, region, layer or section discussed below could be termed a second element, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Some example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit( ) or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

FIG. 1 is an illustration of an aerosol-generating system 100 according to some example embodiments. FIG. 1 is schematic in nature. In particular, the elements shown are not necessarily to scale either individually or relative to one another. As shown in FIG. 1, in some example embodiments the system is a handheld, electrically operated vaping device and may include a housing 110. The housing 110 may at least partially define an interior space, also referred to herein as an interior of the housing 110. The interior space may include a cavity, as discussed further below. Within the housing 110, the aerosol-generating system 100 may include an electric power supply in the form of battery 112 and control circuitry 114 configured to selectively control the supply of electrical power from the electric power supply to one or more elements of the aerosol-generating system 100, including one or more of a vaporizer 134 and a pump 130 included in the aerosol-generating system 100, as described further below.

Also within the interior space of the housing 110, the system 100 may include a liquid reservoir 120 containing a liquid aerosol-forming substrate that may be vaporized in order to form an aerosol.

In some example embodiments, the aerosol-generating system 100 may include an atomizer assembly 130 within the interior space of the housing 110, coupled to the liquid reservoir 120. The atomizer assembly 130 may include a vaporizer 134. As shown in FIG. 1, in some example embodiments, the vaporizer 134 may include an electrical heater, and a pump 132 that is configured to pump liquid from the liquid reservoir 120 to the vaporizer 134. Both the pump 132 and the electric heater of the vaporizer 134 may be configured to receive a supply of electrical power from the power supply 112 under the control of the control circuitry 114, as will be described further below.

The housing 110 includes an air inlet 118 and an air outlet 116. The air outlet 116 is provided at an outlet end of the housing 110. In some example embodiments, the aerosol-generating system 100 is configured to enable an adult vaper to draw on the outlet end of the housing 110, such that air is drawn through the air inlet 118 into the housing 110 interior space, past the vaporizer 134 and out of the interior space and out of the housing 110 through the air outlet 116. The air drawn past the vaporizer 134 may at least partially entrain a generated vapor that is generated based on the vaporizer 134 vaporizing liquid aerosol-forming substrate conveyed to the vaporizer 134 from the liquid reservoir 120. The vaporized aerosol-forming substrate may cool to form an aerosol as it moves through the system 100 interior to the air outlet 116.

Activation of the heater may be controlled directly based on adult vaper interaction with a button included on the housing 110. In some example embodiments, the system 100 may include an airflow sensor 115, such as a microphone, that is configured to detect airflow through the system 100. The control circuitry 114 may be configured to activate the heater included in the vaporizer 134 based on signals generated by the airflow sensor 115. For example, if and when an adult vaper draws air through the system 100, air may flow past (e.g., in fluid communication with) the air flow sensor 115. If and/or when the airflow detected by the airflow sensor 115 exceeds a threshold value, then the control circuitry 114 may selectively “activate” the heater included in the vaporizer 134 based on selectively causing electrical power to be supplied from the power supply 112 to the heater. The control circuitry 114 may cause electrical power to be supplied to the heater for a particular (or, alternatively predetermined) period of elapsed time, may cause electrical power to be supplied to the heater for as long as the detected airflow detected at the airflow sensor 115 exceeds a threshold, some combination thereof, or the like. The control circuitry 114 may include one or more elements configured to sense a temperature associated with one or more portions of the aerosol-generating system 100, including one or more of a dedicated temperature sensor, an element configured to monitor an electrical resistance associated with of the heater, etc. The control circuitry 114 may be configured to cause electrical power to be supplied to the heater to raise the temperature of the heater to within a particular temperature range. The temperature should be sufficient to vaporize the aerosol-forming substrate but not so high that there is a significant risk of combustion.

The pump 132 may be activated in the same way as the heater. For example, the control circuitry 114 may cause electrical power to be supplied to the pump 132 for the same time periods as power is supplied to the heater. In some example embodiments, the control circuitry 114 may cause electrical power to be supplied to the pump 132 in one or more time periods immediately following activation of the heater.

In some example embodiments, the liquid aerosol-forming substrate, also referred to herein as simply the “liquid,” may include a mixture of water, glycerol, propylene glycol, nicotine one or more flavorants, some combination thereof, or the like. The liquid may be held within the liquid reservoir 120. The liquid reservoir 120 may be a cartridge that can be replaced from the system 100. The reservoir 120 may be replaced from the system 100 based on the liquid having been depleted below a threshold amount (e.g., mass, volume, etc.).

In order to prevent leakage of the liquid, in some example embodiments, the liquid reservoir 120 includes a rigid or substantially rigid housing (e.g., a housing that is rigid within manufacturing tolerances and/or material tolerances) that includes (e.g., at least partially comprises) a rigid plastics material, and is liquid tight. As used herein, “rigid” means that the housing is self-supporting. In some example embodiments, the reservoir 120 is formed based at least in part upon 3D printing using an acrylic based photopolymer. The cartridge that includes the reservoir 120 may be robust and configured to withstand significant loads during shipping and storage. In some example embodiments, because the liquid reservoir 120 housing is sealed and rigid, the liquid reservoir 120 has a fixed internal volume. A reduction in the internal pressure inside the liquid reservoir 120 as a result of liquid being removed therefrom by the pump 132, could detrimentally affect the ability to pump liquid out of the reservoir. In order to prevent a significant drop in pressure, the liquid reservoir 120 may include an equalizing air inlet valve 122. The equalizing air inlet valve 122 may enable allows air to flow into the liquid reservoir based on a pressure difference between the interior of the liquid reservoir 120 (e.g., the interior of the housing of the reservoir 120) and the exterior of the reservoir 120 (e.g., a difference between the reservoir internal pressure and the ambient pressure, a difference between the reservoir internal pressure and an internal pressure within the interior space, etc.) at least meets a threshold pressure difference associated with the equalizing air inlet valve 122.

Figure 2:
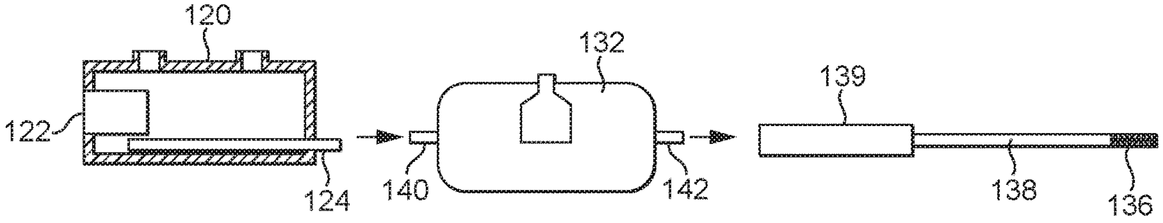
FIG. 2 is a schematic illustration of the elements of a cartridge according to some example embodiments.

FIG. 2 is an exploded view of the liquid reservoir 120, pump 132 and a heater assembly, the heater assembly comprising tube 139, a capillary nozzle 138 and a heater 136 according to some example embodiments. As shown in FIG. 2, the liquid reservoir 120 may include an equalizing air inlet valve 122 and a liquid outlet 124. The liquid outlet 124 may be configured to engage with an inlet 140 of the pump 132. The outlet 124 may be sealed with a removable cap or may be sealed with a pierceable seal.

In some example embodiments, the pump 132 may include a piezoelectric micropump, such as an MP6 pump manufactured by Bartels Mikrotechnik GmbH, Konrad-Adenauer-Allee 11, 44263 Dortmund, Germany (www.bartels-mikrotechnik.de). The pump 132 may include an outlet 142 that is configured to engage with the tube 139 of the heater assembly.

The tube 139 may connect the pump 132 to a capillary nozzle 138. The capillary nozzle 138 may be a 2 ml glass capillary element. A nickel-chromium heater wire may be wound around the capillary nozzle 138 to heat liquid in the capillary nozzle 138.

Figure 3:
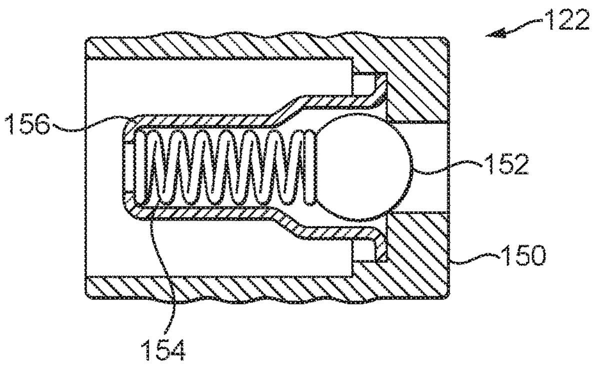
FIG. 3 is a cross sectional illustration of the inlet valve of FIG. 2.

FIG. 3 shows the construction of an equalizing air inlet valve 122, also referred to herein as an inlet valve 122, of FIG. 2 in detail. In some example embodiments, including the example embodiments illustrated in FIG. 3, the inlet valve 122 may be a check valve. In some example embodiments, for example, the inlet valve 122 may be a check valve that is a 5 mm diameter, ceramic ball check valve, manufactured by The Lee Company, 2 Pettipaug Rd, PO Box 424, Westbrook, Conn. 06498-0424 USA. The inlet valve 122 may be configured to be push fit to the reservoir 120 housing. The inlet valve 122 may include a stainless steel body 150 and a stainless steel frame 156. A stainless steel spring 154, seated on the frame 156, may be configured to push the ceramic ball 152 against the body to seal an aperture included in the body. If and/or when a pressure difference across the ball becomes great enough to move the ball against the bias of the spring, the aperture may be unsealed, allowing air into the liquid reservoir 120.

In some example embodiments, the liquid reservoir 120 is a cartridge. The cartridge may be configured to be received in the housing 110 of the system 100. The cartridge may be configured (e.g., "keyed") to ensure that the outlet 124 correctly engages the inlet 140 of the pump 132. The pump 132 and heater assembly 134 may be included in a replaceable atomizer assembly 130. The atomizer assembly may be configured to be received in the housing 110. In some example embodiments, the vaporizer assembly may be integrally included in (e.g., form a part of) the housing 110.

In some example embodiments, the power supply 112 is a lithium iron phosphate battery that is rechargeable. Charging contacts may be provided on the housing 110. The control circuitry 114 may include a programmable microprocessor that is configured to control the supply of electrical power to the heater included in the vaporizer 134 and to the pump 132.

The housing 110 may include (e.g., may be formed from, at least partially include, etc.) polyetheretherketone (PEEK) and may have a size and shape such that the housing 110 is configured to be comfortable for an adult \Taper to hold in a single hand. The system 100 may include a removable outlet end around the outlet 116. The outlet end piece may be configured to be removably coupled to a remainder of the system 100, such that the outlet end piece may be removed to allow access to a cavity (e.g., interior space) in the housing 110 in which the cartridge that at least partially comprises the liquid reservoir 120 and vaporizer 134 is held (e.g., an interior of the housing 110).

In some example embodiments, the main housing 110, the atomizer assembly and the liquid reservoir 120 cartridge of the system 100 may be assembled together to establish the system 100 prior to operation of the system 100.

In order to activate the system, may include a button on the housing 110 may be pressed based on adult vaper interaction therewith. In some example embodiments, based on adult vaper interaction with the system 100, the control circuitry 114 may cause electrical power to be supplied from the power supply 112 to the pump 132 so that liquid is pumped to the heater assembly included in the vaporizer 134. Air may then be drawn through the system 100 via the outlet 116.

The system 100 may include an airflow sensor 115, which may include a microphone that is configured to detect a flow of air through the system 100. The air flow that flows in fluid communication with the airflow sensor 115 may enter the system 100 through an auxiliary air inlet 117 that is much smaller than air inlet 118. Based on (e.g., in response to) a signal generated by the airflow sensor 115, the control circuitry 114 may cause electrical power to be supplied from the power supply 112 to the heater 136 so that the heater heats up and vaporizes the liquid in the capillary nozzle 138. The vaporized liquid aerosol-forming substrate may then cool in the airflow and condense to form an aerosol that is drawn out of the system 100. In some example embodiments, the control circuitry 114 may cause electrical power to be supplied to a heater for a fixed or substantially fixed duration (e.g., a duration that is fixed within manufacturing tolerances and/or material tolerances) following detection of an airflow through the system that at least meets a threshold flow. Various control schemes for the supply of electrical power to a heater may be used. Electrical power may be supplied to the pump for the same period or substantially same period that electrical power is supplied to the heater in order to replenish the liquid in the nozzle 138 as it is being vaporized. When an adult vapor has finished using the system they can switch the system off using a button. In some example embodiments, the control circuitry 114 may be configured to switch the system off if based on a determination that at least the threshold flow is absent for at least a particular (or, alternatively predetermined) period of elapsed time.

As liquid is drawn out of the liquid reservoir by the pump 132, the valve 122 may open to equalize the pressure inside the reservoir (e.g., reservoir internal pressure) with the pressure outside of the reservoir (e.g., ambient pressure). The valve may include a covering baffle, such that the valve is configured to reduce a flow of aerosol back into the reservoir 120 during the generation of aerosol and/or the drawing of air through the system 100.

Figure 4:
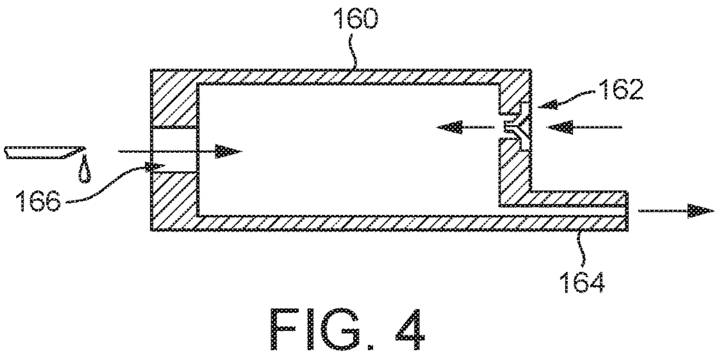
FIG. 4 is a schematic illustration of another embodiment of a cartridge according to some example embodiments.

Example embodiments described with reference to FIGS. 2 and 3 are some example embodiments of an aerosol-generating system 100 according to some example embodiments. FIG. 4 shows a liquid reservoir and valve configuration according to some example embodiments. The liquid reservoir of FIG. 4 is a refillable reservoir. The liquid reservoir shown in FIG. 4 includes a rigid, generally cylindrical housing 160 and has a liquid outlet 164 configured to engage a pump and an equalizing valve 162. The equalizing valve in the example embodiments shown in FIG. 4 is a duckbill valve configured to allow air into the liquid reservoir when the pressure difference between the reservoir interior and the reservoir exterior exceeds a threshold pressure difference. The liquid reservoir may include a filling port through which the liquid reservoir may be refilled with liquid aerosol-forming substrate. The filling port may be sealed by an elastomeric septum 166. In order to refill the liquid reservoir, the septum 166 may be pierced by a needle and liquid injected through the needle into the liquid reservoir.

It is also possible to use alternative vaporizers to the heater described with reference to FIG. 2. For example, a vaporizer may include a heated mesh or a vibrating mesh, with the pump configured to deliver liquid to the interstices of the mesh. The vaporizer may include a heated plate or pair of plates and the pump 132 may deliver liquid to the plate or plates. The vaporizer may be an inductively heated element.

In some example embodiments, a system 100 may include one or more various configurations (e.g., "arrangements") of the elements thereof, including one or more various configurations that may be separate from the configuration of elements shown in FIG. 1. Systems 100 including one or more various configurations of elements thereof may include one or more various configurations of elements that define one or more various airflow paths through the system. For example, in some example embodiments, the system 100 may include an atomizer assembly that is closer to the outlet end of the system 100 than the liquid reservoir 120. The system may include one or more air inlets, airflow sensors, some combination thereof, or the like in one or more various configurations, arrangements, positions, etc. in the system 100.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

What is claimed is:

1. A cartridge for an electrically operated aerosol-generating system, the cartridge comprising:

a reservoir configured to hold a liquid aerosol-forming substrate, the reservoir including a rigid housing that includes a filling port, the filling port being sealed and configured to direct the liquid aerosol-forming substrate into an interior of the reservoir, an air inlet valve configured to allow air into the reservoir based on a pressure difference between the interior of the reservoir and an exterior of the reservoir exceeding a threshold pressure difference, and an outlet extending through the rigid housing, the outlet including a pierceable seal;

a vaporizer configured to vaporize the liquid aerosol-forming substrate; and a pump configured to engage with the vaporizer to convey liquid aerosol-forming substrate from the reservoir to the vaporizer, the pump being between the reservoir and the vaporizer, and the outlet of the reservoir being configured to detachably engage with the pump, such that the pierceable seal of the outlet is pierced by the pump and the outlet of the reservoir directs the liquid aerosol-forming substrate out of the reservoir.

2. The cartridge according to claim 1, wherein the filling port is sealed by a pierceable septum.

3. The cartridge according to claim 1, wherein the outlet is configured to be sealed prior to engagement with the pump.

4. The cartridge according to claim 1, wherein the filling port is sealed by a removable plug.

5. The cartridge according to claim 1, wherein the vaporizer includes an electrical heater.

6. The cartridge according to claim 5, wherein the vaporizer includes a capillary material configured to convey liquid aerosol-forming substrate to the electrical heater.

7. The cartridge according to claim 1, wherein the pump is a piezoelectric micropump.

8. The cartridge according to claim 1, wherein the air inlet valve is a check valve.

9. The cartridge according to claim 8, wherein the check valve is one of a ball check valve and a duckbill check valve.

10. An electrically operated aerosol-generating system comprising:

a housing configured to define an interior space, the housing including, an air inlet configured to direct air into the interior space of the housing, and an air outlet configured to direct at least air out of the interior space of the housing;

a cartridge within the interior space of the housing, the cartridge including, a liquid reservoir configured to hold a liquid aerosol-forming substrate, the liquid reservoir including a rigid housing that includes a filling port, the filling port being sealed and configured to direct the liquid aerosol-forming substrate into an interior of the liquid reservoir, an air inlet valve configured to allow air into the liquid reservoir from the interior space of the housing of the aerosol-generating system based on a pressure difference between the interior of the liquid reservoir and an exterior of the liquid reservoir exceeding a threshold pressure difference, and an outlet extending through the rigid housing, the outlet including a pierceable seal;

a vaporizer within the interior of the housing, the vaporizer configured to vaporize the liquid aerosol-forming substrate; and a pump connected to the outlet of the cartridge, the pump configured to convey liquid aerosol-forming substrate from the liquid reservoir to the vaporizer, the pump being between the liquid reservoir and the vaporizer, and the outlet of the liquid reservoir being configured to detachably engage with the pump, such that the pierceable seal of the outlet is pierced by the pump and the outlet of the liquid reservoir directs the liquid aerosol-forming substrate out of the liquid reservoir.

11. The aerosol-generating system according to claim 10, wherein the filling port is sealed by a pierceable septum.

12. The aerosol-generating system according to claim 10, wherein the air inlet valve is a check valve.

13. The aerosol-generating system according to claim 10, wherein the pump is a piezoelectric micropump.

14. The aerosol-generating system according to claim 10, wherein the vaporizer includes an electrical heater.

15. The aerosol-generating system according to claim 10, further comprising:

a power supply configured to supply electrical power to the pump and the vaporizer.

16. The aerosol-generating system according to claim 10, further comprising:

control circuitry configured to activate the pump based on a determination that the vaporizer is activated.

17. The aerosol-generating system according to claim 10, wherein the aerosol-generating system is a hand held electronic vaping device.

18. A method, comprising:

detachably engaging a reservoir with a pump via an outlet of the reservoir such that a seal of the outlet of the reservoir is pierced by the pump, the reservoir including a rigid housing held within a housing of an aerosol-generating system and configured to hold a liquid aerosol-forming substrate, the outlet extending through the rigid housing and being configured to direct the liquid aerosol-forming substrate out of the reservoir;

engaging a vaporizer with the pump to convey the liquid aerosol-forming substrate from the reservoir to the vaporizer, the pump being between the reservoir and the vaporizer;

conveying the liquid aerosol-forming substrate out of the reservoir based on operation of the pump, the conveying including conveying the liquid aerosol-forming substrate through the outlet from the reservoir to the vaporizer, the vaporizer being configured to vaporize the liquid aerosol-forming substrate based on generating heat;

allowing air into the reservoir from an interior of the housing of the aerosol-generating system through the rigid housing based on a pressure difference between an interior of the reservoir and an exterior of the reservoir exceeding a threshold pressure difference;

piercing a seal of a filling port of the rigid housing; and directing the liquid aerosol-forming substrate into the interior of the reservoir via the filing port.

19. The method of claim 18, wherein the conveying further includes, selectively controlling a particular supply of electrical power to the pump based on a determination that the vaporizer is activated.

20. The method of claim 19, wherein the conveying further includes, selectively controlling a separate supply of electrical power to the vaporizer, such that the vaporizer is activated, based on a determination that a flow rate of air detected by a flow sensor exceeds a threshold flow rate.

* * * * *